United States Patent [19]
Park

[11] Patent Number: 5,886,358
[45] Date of Patent: Mar. 23, 1999

[54] DEVICE FOR DETECTING CUT OF A TAPE HAVING ENGAGED GEAR DETECTING MEANS

[75] Inventor: Bong-Hwan Park, Incheon, Rep. of Korea

[73] Assignee: Daewoo Electronics, Co., Ltd., Seoul, Rep. of Korea

[21] Appl. No.: 722,529

[22] Filed: Sep. 27, 1996

[30] Foreign Application Priority Data

Sep. 29, 1995 [KR] Rep. of Korea ............... 1995-32828

[51] Int. Cl.$^6$ .................................................. G01N 21/86
[52] U.S. Cl. ............................. 250/559.45; 250/559.42
[58] Field of Search ........................... 250/559.45, 559.4, 250/559.43, 559.42, 223 R, 223 B; 396/512, 514, 515; 360/72.3, 74.2, 73.11, 74.3

[56] References Cited

U.S. PATENT DOCUMENTS 3,746,784  7/1973  Van Oosterhout ................. 250/223 B

*Primary Examiner*—Que T. Le
*Attorney, Agent, or Firm*—Sixbey, Friedman Leedom & Ferguson; Frank P. Hresta; Joseph S. Presta

[57] ABSTRACT

A device for detecting cut of a tape generates a cut signal of a tape by using a pulse generating portion and a light signal generating portion when a number of pulses per second generated by the rotation of a detecting gear is larger than the maximum number of pulses per second during normal operation. A first gear is rotated by a rotation driving part in forward play operation mode of a tape. A second gear is rotated by the rotation driving part in reverse play operation mode of the tape. A detecting gear of a detecting gear portion is engaged with the first gear or the second gear according to the operation mode. A pulse generating portion generates pulses corresponding to a speed of revolution of the detecting gear and a light signal generating and pulse detecting portion detects the generated pulses. A microprocessor decides the revolution state of the engaged gear from the number of detected pulses per second.

7 Claims, 4 Drawing Sheets

DEVICE FOR DETECTING CUT OF A TAPE HAVING ENGAGED GEAR DETECTING MEANS

BACKGROUND OF THE INVENTION

1. Field of the Invention

The present invention relates to a device for detecting cut of a tape, particularly to a device for detecting cut of a tape for promptly detecting cut of a tape by detecting a difference of a revolution speed of a gear according to a tape state.

2. Description of the Prior Art

Conventionally, apparatuses like a video tape recorder, an audio tape recorder, and a reel tape reader comprise a driving system for rotating a tape reel. The driving system comprises a forward reel gear for operating a forward play mode of a tape and a reverse reel gear for reverse playing the tape. Each gear operates as a main rotating reel gear or a follower gear according to an operation mode. The tape is wound in a forward direction or a reverse direction according to the rotation of the main rotating reel gear.

In these apparatuses, a microcomputer is used for controlling a rotation of the main rotation reel gear. The microcomputer controls the main rotation reel gear to stop the rotation when a stop signal or an end signal is inputted. If the tape is cut during the operation mode, the main rotation reel gear connected with the driving system continues to rotate but the following reel gear unconnected with the driving system stops rotating because the state of the tape being cut is unrecognized. As a result, a user waits to start the operation mode for a long time frequently because the microcomputer does not recognize that the tape is cut. Thus, various apparatuses and methods for detecting a cut of a tape are proposed to detect the cut of the tape.

FIG. 1 is a schematic diagram of one conventional apparatus for detecting cut of a tape. The apparatus for detecting cut of a tape comprises a forward reel gear 100 to be rotated by a rotation driving part(not shown) during the forward play operation mode of the tape and a reverse reel gear 200 to be rotated by the rotation driving part during the reverse play operation mode of the tape. Forward reel gear 100 comprises a first photoelectric pulse generator. The first photoelectric pulse generator comprises a first rotating plate 110 to be rotated according to the rotation of forward reel gear 100 and a first photo sensor 120 installed at a predetermined position in a lower direction of first rotating plate 110. First rotating plate 110 comprises four first light reflecting portions 112 for reflecting light outputted from first light sensor 120 and four first absorbing portions 114 for absorbing the light.

Reverse reel gear 200 comprises a second photoelectric pulse generator. The second photoelectric pulse generator comprises a, second rotating plate 210 to be rotated according to the rotation of reverse reel gear 200 and a second light sensor 220 installed at a predetermined position in a lower direction of second rotating plate 120. Second rotating plate 210 comprises four second light deflection portions 212 for reflecting the light outputted from second light sensor 220 and four second absorbing portions 214 for absorbing the light.

An operation of the conventional device for detecting cut of the tape according to a construction described above is described below with reference to FIG. 1 and FIG. 2.

The microcomputer(not shown) detects the presence of an input signal(S1). When the input signal is present, the microcomputer operates first and second light sensors 120, 220.

Next, the microcomputer decides whether the input signal is to indicate the forward play operation mode(S3). If a result of the decision is true, the rotation driving part(not shown) is connected to forward reel gear 100 because forward reel gear 100 is the main reel gear(S4). If the result is false, the rotation driving part is connected to reverse reel gear 200 because reverse reel gear 200 is the main reel gear(S5).

The tape is wound around the circumferential face of the main rotating reel gear when the main reel is rotated by the rotation driving part. The following reel gear is rotated because the tape is wound around the main rotating reel gear.

Lights outputted from first and second light sensor 120, 220 arrive at first and second rotating plates 110, 210 according to the rotation of the main rotation reel gear and the following reel gear, and thus pulses are generated. The microcomputer counts a pulse repetition rate(P1) generated according to the rotation of the main rotating reel gear and a pulse repetition rate(P2) generated according to the rotation of the following reel gear(S5).

With cut of the tape, the main reel gear continues to rotate by the rotation driving part, and the following reel gear continues to rotate by inertia because the following reel gear is unconnected with the rotation driving part. Thus, the microcomputer checks whether P2 equals zero because the following reel gear is stopped(S6) first. When P2 equals zero, the microcomputer outputs a signal of the cut of the tape by deciding the tape cut state(S7). When P2 is unequal to zero, the microcomputer counts the pulses generated by the rotation of the reel gears.

When the input signal is not a signal for indicating the forward play operation mode, the microcomputer connects the rotation driving part to reverse reel gear 200 because reverse reel gear 200 is the main rotation reel gear. After that the operation operates in described order.

A conventional device for detecting cut of the tape has a complicated construction because first and second photoelectric pulse generators are installed at forward reel gear 100 and reverse reel gear 200 for counting pulses generated according to the rotation of forward reel gear 100 and reverse reel gear 200.

Also, in an operation mode, when tape is cut, the main rotation reel gear continues to rotate by the rotation driving part and the following reel gear continues to rotate by inertia. Thus, the time for detection is long because cut of the tape is detected after the following reel gear completely stops to rotate.

SUMMARY OF THE INVENTION

Therefore, it is an object of the present invention to provide a simple device for detecting cut of a tape comprising a pulse generating portion and light signal generating and pulse detecting portion.

It is another object of the present invention to provide a device for detecting cut of a tape for promptly indicating cut state of the tape when the tape is cut during the operation mode by detecting a difference of the revolution speed of the gears according to the tape state.

To accomplish the above objects of the present invention, there is provided a disk clamping device in the present invention that comprises a first gear rotated by a rotating driving portion in a forward play operation mode, a second gear rotated by the rotating driving portion in a reverse play operation mode of the tape, and a detecting gear part for detecting a rotation state of a gear selectively engaged with the first gear or second gear according to the operation mode.

The detecting gear part comprises a detecting gear, a first connecting gear, a second connecting gear, a pulse generating portion, a light signal generating and pulse detecting portion, and a microprocessor. The detecting gear rotates according to the rotation of the engaged gear because the detecting gear is engaged with the first gear through the first connecting gear or is engaged with the second gear through the second connecting gear according to the operation mode. The pulse generating portion is fixed and installed at the detecting gear, and comprises a reflecting portion and an absorbing portion. The pulse generating portion generates the pulses corresponding to the rotating velocity of the detecting gear because the reflecting portion and the absorbing portion are arranged radially and alternatingly.

The device for detecting cut of a tape has a simple construction for detecting cut of a tape by using a pulse generating portion and light signal generating and pulse detecting portion.

Also the device for detecting cut of a tape according to the present invention detects a signal of the tape cut by deciding whether the rotating velocity of the detecting gear portion is within range of the rotating velocity during normal operation condition when the detecting gear portion is selectively engaged with the first gear or the second gear. That is, a signal of the tape cut is generated by deciding the tape cut state when the generated number of pulses according to the rotation of the detecting gear is larger than the maximum number of pulses generated in the normal operation. Thus, an interval between a starting time of the tape cut and a generating time of the tape cut is quite shortened. Consequently, information of an erroneous operation is promptly provided.

BRIEF DESCRIPTION OF THE DRAWINGS

The properties and virtues of the present invention will become more apparent by detailedly describing a preferred embodiment with reference to the attached drawings in which.

DETAILED DESCRIPTION OF THE PREFERRED EMBODIMENT

The construction of the device for detecting cut of a tape of the present invention will be described in detail with reference to FIG. 3.

Figure 1:
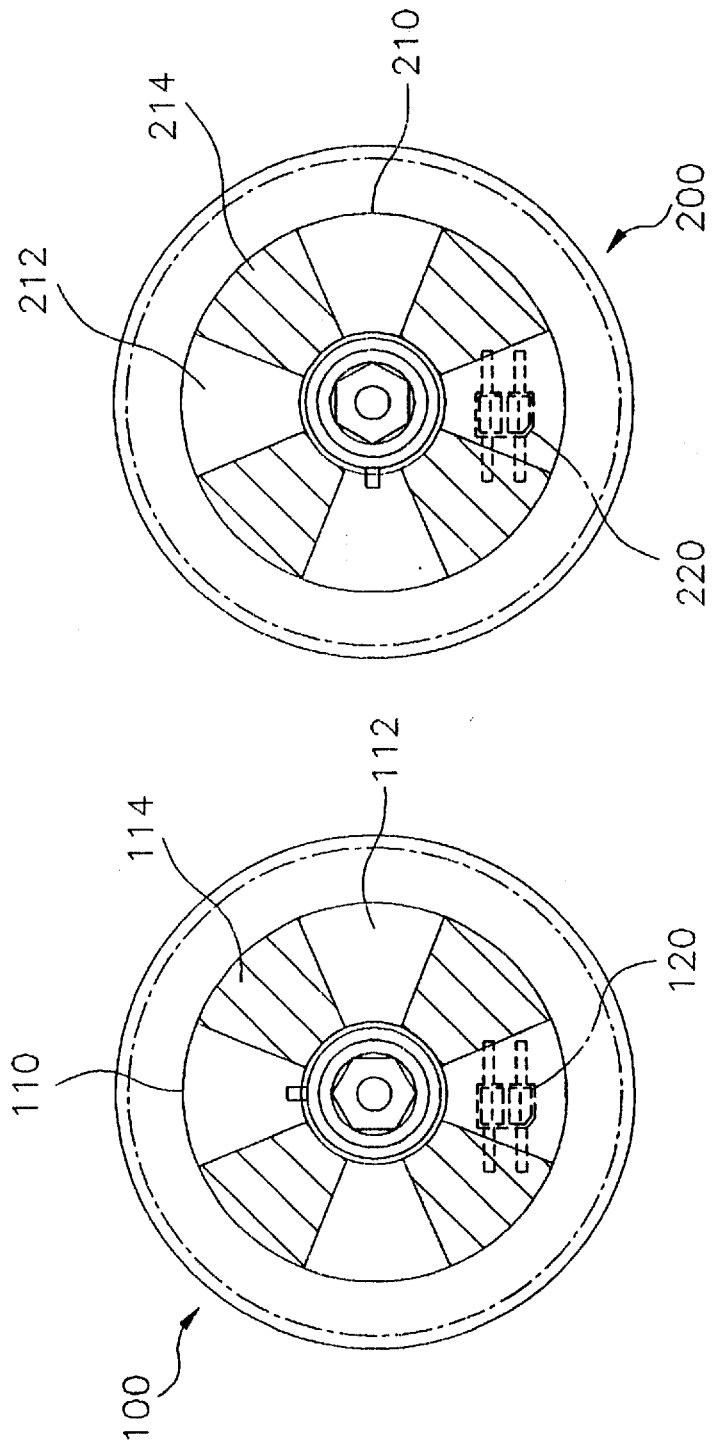
FIG. 1 is a schematic view of a conventional device for detecting cut of a tape.
Figure 2:
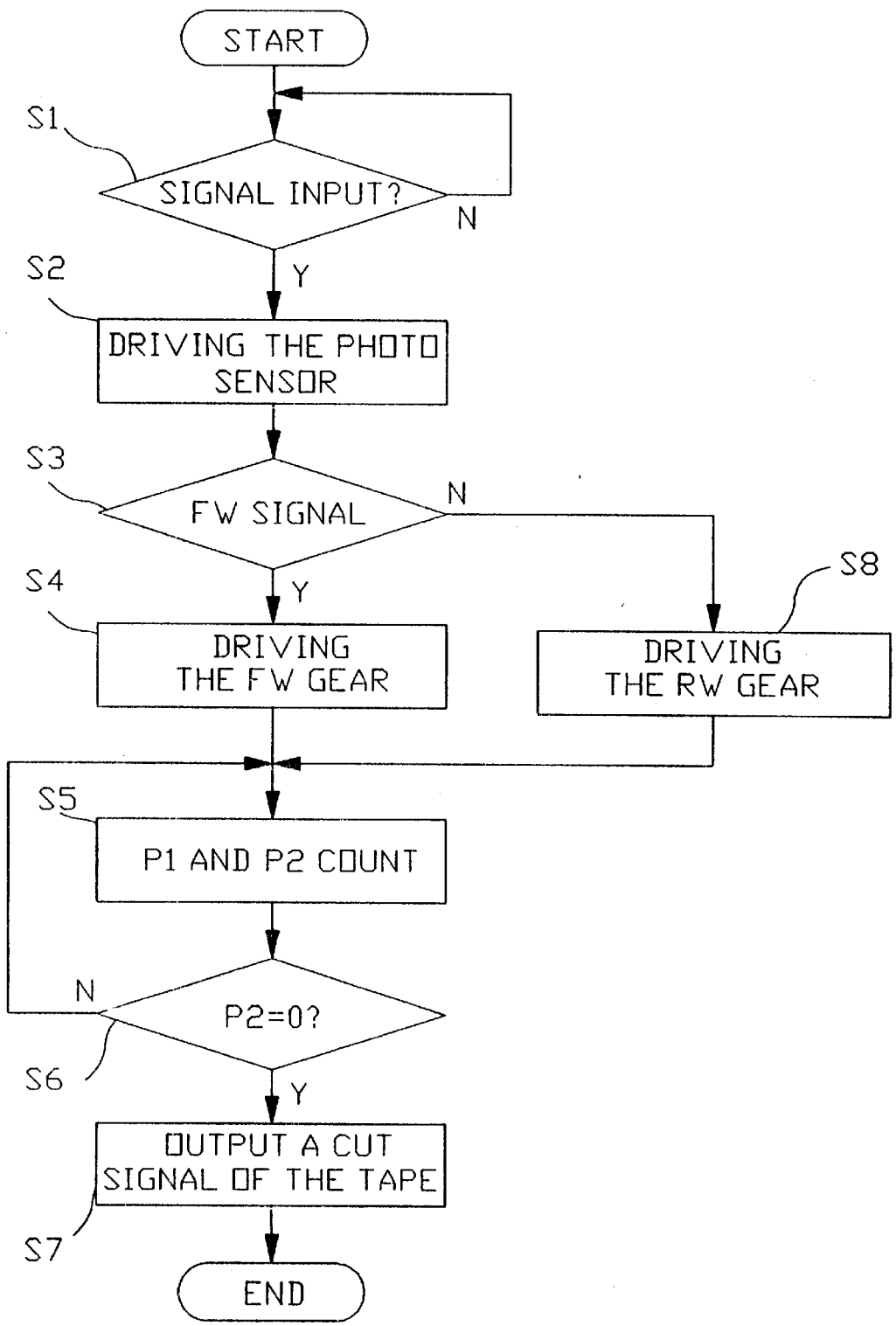
FIG. 2 is a flowchart showing a step for detecting cut of the tape in conventional device for detecting cut of the tape.
Figure 3:
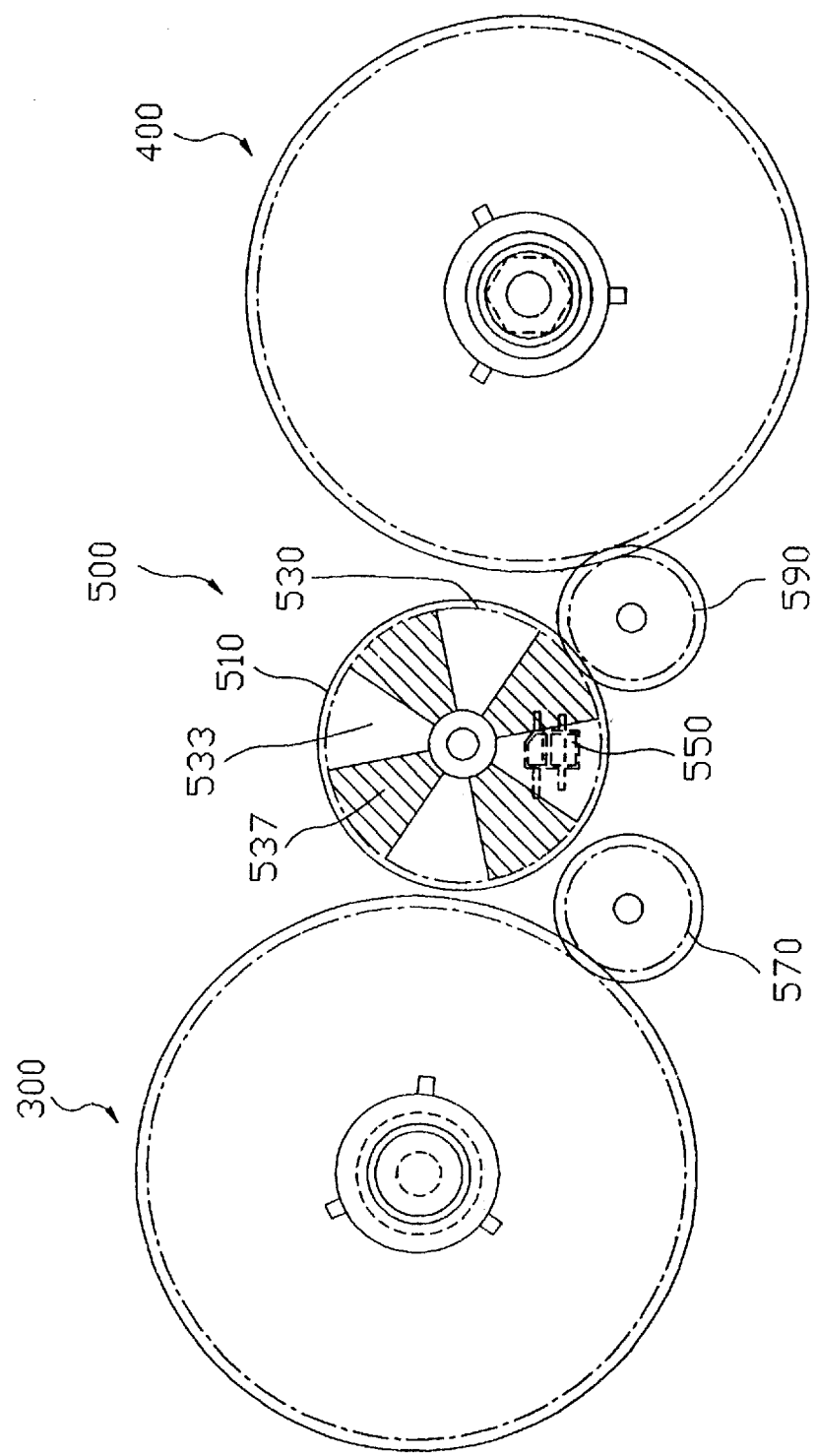
FIG. 3 is a schematic view of a device for detecting cut of a tape according to the present invention.
Figure 4:
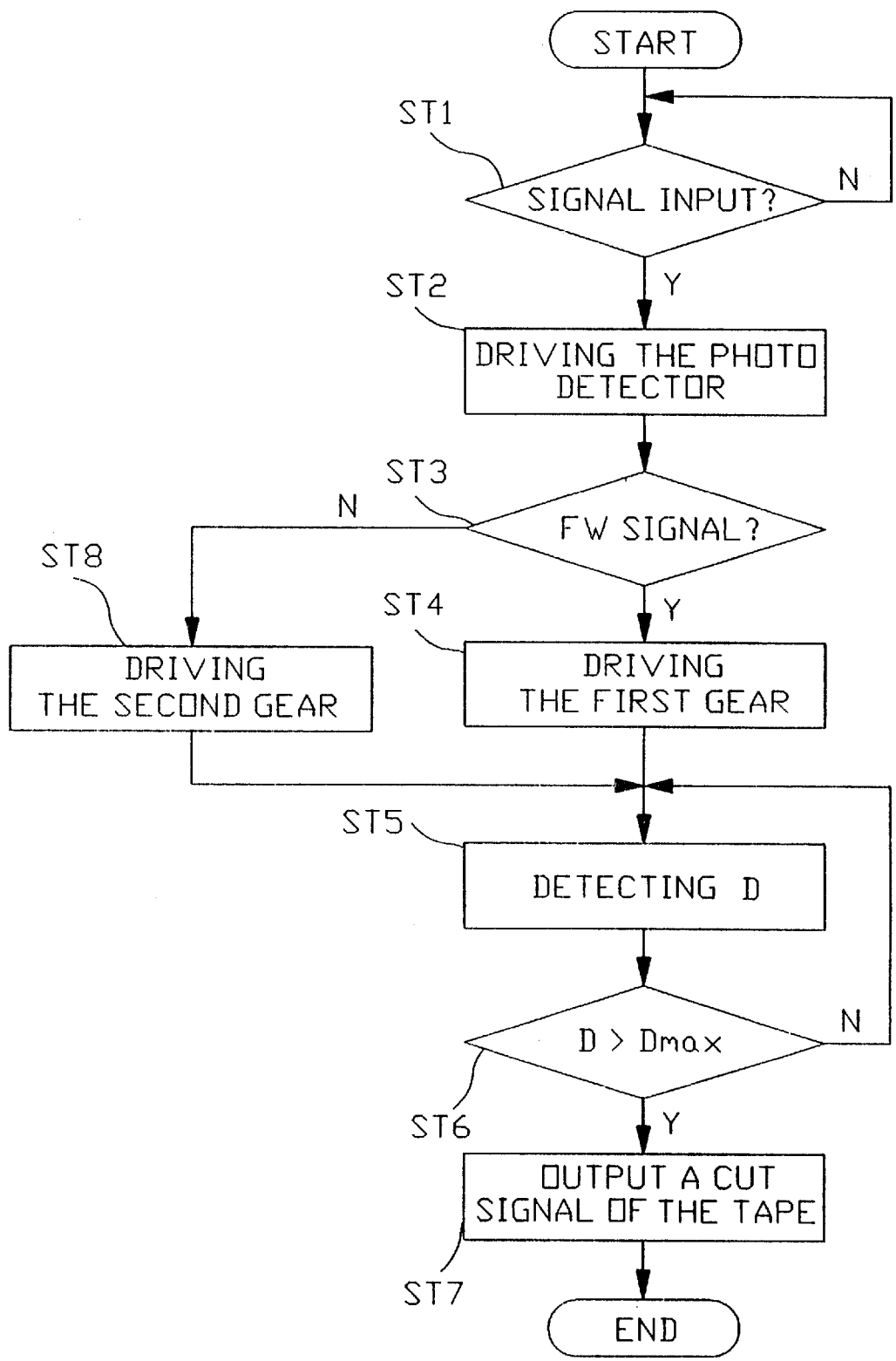
FIG. 4 is a flowchart showing the step for detecting cut of the tape according to the present invention.

As shown in FIG. 3, the device for detecting cut of the tape comprises a first gear 300, a second gear 400, and a detecting gear portion 500. First gear 300 and second gear 400 are rotated by a rotation driving part(not shown) selectively connected with each gear according to the operation mode.

Detecting gear portion 500 is installed at a position between first gear 300 and second gear 400 for detecting a rotating velocity of first gear 300 or second gear 400 according to the operation mode. Detecting gear portion 500 comprises a detecting gear 510, a first connecting gear 570, a second connecting gear 590, a pulse generating portion 530, a light signal generating and pulse detecting portion, and a microprocessor(not shown). Light signal generating and pulse detecting portion 550 is a photo detector.

First connecting gear 570 engages first gear 300 with detecting gear 510 in the forward play operation mode. Second connecting gear 590 engages second gear 400 with detecting gear 510 in the reverse play operation mode.

Detecting gear 510 rotates according to the rotation of first gear 300 because detecting gear 510 engages first gear 300 through first connecting gear 570 in the forward play operation mode. Also, detecting gear 510 rotates according to the rotation of second gear 400 because detecting gear 510 engages second gear 400 through second connecting gear 590.

Pulse generating portion 530 is fixedly installed at detecting gear 510 for generating pulses according to the rotation of detecting gear 510. Pulse generating portion 530 comprises four reflecting portions 533 for reflecting a light beam emitted from light signal generating and pulse detecting portion 550 and four absorbing portions 537 for absorbing the light beam to detect the number of rotations of detecting gear 510. Reflecting portions 533 and absorbing portions 537 are alternatingly arranged in a radial direction.

Light signal generating and pulse detecting portion 550 is installed to emit the light beam toward pulse generating portion 530 and to receive the pulses generated from pulse generating portion 530 according to the rotation of detecting gear 510 by using the light beam.

The microprocessor(not shown) decides the rotating state of the gear engaged with detecting gear portion 500 by using the number of pulses detected by light signal generating and pulse detecting portion 550.

Detailed descriptions will be given for the operations of the device for detecting cut of a tape according to an embodiment of the present invention.

When the tape is installed in the device, then the forward play operation signal is inputted to the microcomputer(ST1). The microcomputer then drives the photo detector(ST2). The microcomputer decides whether the inputted signal is the forward play signal(ST3). When the inputted signal is the forward play signal, the rotation driving part connects with first gear 510 so that first connecting gear 570 engages first gear 300 with detecting gear(ST4). First gear 300 rotates in counterclockwise direction according to the rotation of the rotation driving part. First connecting gear 570 rotates in clockwise direction according to the rotation of first gear 300. Detecting gear 510 of detecting gear portion 500 rotates in counterclockwise direction according to the rotation of first connecting gear 570.

According to the rotation of detecting gear 510, the light beam emitted from light signal generating and pulse detecting portion 550 emits the light beam toward pulse generating portion 530, and then the light beam arrives at a point of pulse generating portion 530. The light pulses are generated by reflecting portion 533 and absorbing portion 537 due to rotation of pulse generating portion 530, and the generated light pulses are inputted in light signal generating and pulse detecting portion 550.

In normal operation mode, that is, in forward operation mode, the number of rotations during one minute of detecting gear 510 rotation according to the rotation of first gear 300 is the maximum value, for example, 87 rpm, when the operation mode commences the operation, and is the minimum value, for example, 38 rpm, when the operation mode has finished the operation.

Thus, the number of pulses per second detected in light signal generating and pulse detecting portion 550 according to the rotation of first gear 300 is the maximum value(Dmax) in the starting point of operation mode and is the minimum value(Dmin) in the finishing point. Because pulse generating portion 530 of the present invention uses four reflecting portions 533 and four absorbing portions 537, the number of pulses detected for a second(D) is the value between 2.5 (Dmin) and 5.8(Dmax).

While during abnormal operation, that is, with the tape being cut, the speed of revolution of first gear 300 rotates faster than the speed of the normal operation without tension. The speed of revolution for a minute of detecting gear D is, for example, 284 rpm. Therefore, the number of pulses for a second D detected by using light signal generating and pulse detecting portion 550 is 18.9. This value is treble the maximum value Dmax generated in normal operation.

Thus, the microprocessor counts the pulses generated by the rotation of detecting gear 510(ST5). Then, the microprocessor compares the counted number of the pulses to Dmax, for example, 10(ST6). If the counted number is larger than Dmax, the microcomputer generates the signal of the tape cut (ST7).

When the inputted signal is the reverse play operation signal, the rotation driving part connects to second gear 400, and second connecting gear 500 connects second gear 400 to detecting gear 510(ST8).

The device for detecting cut of the tape of the present invention has a simple construction due to using a pulse generating portion and light signal generating and pulse detecting portion to detect the number of rotations of detecting gear rotated by the rotation of first gear or second gear selectively engaged according to the operation mode.

The time required for detecting cut of the tape is long because the conventional device for detecting cut of the tape determines there is a cut state of the tape when the rotation of the following reel gear between the forward reel gear and the reverse reel gear completely stops. The device for detecting cut of the tape of the present invention promptly detects a signal of the tape cut by distinguishing whether the speed of revolution of the detecting gear is the value within a range of the revolution speed during normal operation when the detecting gear portion selectively engages with the rotated gear of the first gear or second gear according to the operation mode. That is, the signal of the tape cut is generated when the number of pulses generated by the rotation of the detecting gear is larger than the maximum number of pulses generated in normal operation. Therefore, an interval between the time of the tape cut and the time generating a signal of the tape cut is short. Thus, the information about the abnormal operation is promptly provided.

While the present invention has been particularly shown and described with reference to particular embodiments thereof, it will be understood by those skilled in the art that various changes in form and details may be effected therein without departing from the spirit and scope of the invention as defined by the appended claims.

What is claimed is:

1. A device for detecting cut of a tape comprising:
   a first gear rotated by a rotation driving means for forward playing the tape in forward play operation mode;
   a second gear rotated by said rotation driving means for reverse playing the tape in reverse play operation mode; and
   a detecting gear means selectively engaged with said first gear or second gear according to the operation mode for detecting a rotation state of the engaged gear,
   wherein said detecting gear means comprises:
      a detecting gear for rotating according to a rotation of the engaged gear;
      a pulse generating means for generating pulses corresponding to the speed of revolution of said detecting gear;
      a light signal generating and pulse detecting means for emitting a light beam toward said pulse;
      means and receiving the pulse generated by said light beam from said pulse generating means; and
      a microprocessor for deciding a rotation state of said engaged gear from pulses detected by said light signal generating and pulse detecting means.

2. The device for detecting cut of a tape as claimed in claim 1, wherein said microprocessor generates a cut signal of the tape when a number of pulses per second detected by said pulse detecting means are larger than the number of pulses per second generated by the rotation of said detecting gear during normal operation.

3. The device for detecting cut of a tape as claimed in claim 1, wherein said pulse generating means is fixedly installed at said detecting gear, comprises a reflecting means for reflecting said light beam and an absorbing means for absorbing said light beam, and generates pulses corresponding to the speed of the rotation when said detecting gear is rotated because said reflecting means and said absorbing means are alternatingly arranged in a radial direction.

4. The device for detecting cut of a tape claimed in claim 3, wherein the number of said reflecting means may be more than one.

5. The device for detecting cut of a tape claimed in claim 3, wherein the number of said absorbing means may be more than one.

6. A device for detecting cut of a tape comprising: a first gear rotated by a rotation driving means for forward playing the tape in forward play operation mode;
   a second gear rotated by said rotation driving means for reverse playing the tape in reverse play operation mode; and
   a detecting gear means selectively engaged with said first gear or second gear according to the operation mode for detecting a rotation state of the engaged gear;
   wherein said detecting gear means comprises:
      a detecting gear for rotating according to a rotation of the engaged gear;
      a pulse generating means being fixedly installed at said detecting gear, comprising a reflecting means for reflecting said light beam and an absorbing means for absorbing said light beam, and generating pulses corresponding to the speed of the rotation when said detecting gear is rotated because said reflecting means and said absorbing means are alternatingly arranged in a radial direction;
      a light signal generating and pulse detecting means for emitting a light beam toward said pulse generating means and receiving the pulse generated by said light beam from said pulse generating means; and
      a microprocessor for generating a cut signal of the tape when a number of pulses detected during one second by said pulse detecting means is larger than the number of pulses generated during one second by the rotation of said detecting gear in normal operation.

7. A device for detecting cut of a tape comprising:
   a first gear rotated by a rotation driving means for forward playing the tape in forward play operation mode;
   a second gear rotated by said rotation driving means for reverse playing the tape in reverse play operation mode; and a detecting gear means selectively engaged with said first gear or second gear according to the operation mode for detecting a rotation state of the engaged gear;

wherein said detecting gear means comprises:

a detecting gear for rotating according to a rotation of the engaged gear;

a first connecting gear for engaging said first gear with said detecting gear according to the operation mode;

a second connecting gear for engaging said second gear with said detecting gear according to the operation mode;

a pulse generating means being fixedly installed at said detecting gear, comprising a reflecting means for reflecting said light beam and an absorbing means for absorbing said light beam, and generating pulses corresponding to the speed of the rotation when said detecting gear is rotated because said reflecting means and said absorbing means are alternatingly arranged in a radial direction;

a light signal generating and pulse detecting means for emitting a light beam toward said pulse generating means and receiving the pulse generated by said light beam from said pulse generating means; and a microprocessor for generating a cut signal of the tape when a number of pulses per second detected by said pulse detecting means is larger than the number of pulses per second generated by the rotation of said detecting gear in normal operation.

* * * * *